United States Patent
Hoffa

(10) Patent No.: US 9,265,907 B2
(45) Date of Patent: Feb. 23, 2016

(54) SELF-CENTERING TRACHEOSTOMY TUBE

(75) Inventor: Andrew K. Hoffa, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1703 days.

(21) Appl. No.: 12/345,973

(22) Filed: Dec. 30, 2008

(65) Prior Publication Data
US 2010/0163050 A1  Jul. 1, 2010

(51) Int. Cl.
*A61M 16/00* (2006.01)
*A62B 9/06* (2006.01)
*A61M 16/04* (2006.01)

(52) U.S. Cl.
CPC ....... *A61M 16/0465* (2013.01); *A61M 16/0434* (2013.01); *A61M 2205/32* (2013.01)

(58) Field of Classification Search
USPC ............................ 128/200.26, 207.14–207.18
See application file for complete search history.

(56) References Cited

U.S. PATENT DOCUMENTS

| | | | |
|---|---|---|---|
| 3,880,168 A * | 4/1975 | Berman | 128/207.15 |
| 3,884,242 A * | 5/1975 | Bazell et al. | 128/207.15 |
| 4,033,353 A * | 7/1977 | La Rosa | 128/207.15 |
| 4,987,895 A * | 1/1991 | Heimlich | 128/207.14 |
| 5,045,072 A * | 9/1991 | Castillo et al. | 604/529 |
| 5,217,005 A | 6/1993 | Weinstein | 128/200.26 |
| 5,308,342 A * | 5/1994 | Sepetka et al. | 604/525 |
| 5,316,706 A * | 5/1994 | Muni et al. | 264/472 |
| 5,653,230 A | 8/1997 | Ciaglia et al. | 128/207.15 |
| 5,749,357 A | 5/1998 | Linder | 128/200.26 |
| 5,983,895 A | 11/1999 | Turner | 128/207.14 |
| 6,135,992 A * | 10/2000 | Wang | 604/525 |
| 6,637,435 B2 | 10/2003 | Ciaglia et al. | 128/207.29 |
| 6,662,804 B2 | 12/2003 | Ortiz | 128/207.14 |
| 6,698,428 B2 * | 3/2004 | Brain | 128/207.14 |
| 2005/0103332 A1 | 5/2005 | Gingles et al. | 128/200.24 |
| 2008/0216839 A1 * | 9/2008 | Rutter | 128/207.14 |

FOREIGN PATENT DOCUMENTS

| | | | |
|---|---|---|---|
| EP | 1923090 A2 | 5/2008 | A61M 16/04 |
| FR | 2 692 789 | 12/1993 | A61M 16/04 |

* cited by examiner

*Primary Examiner* — Oren Ginsberg
(74) *Attorney, Agent, or Firm* — Brinks Gilson & Lione

(57) ABSTRACT

A self-centering tube for providing an air passageway through an opening in a tracheal wall of a patient includes a shaft having a proximal end and a distal end, and a curve along a length of the shaft. At least the distal end and the curve are sized for passage through the opening into an interior space of the trachea of the patient. The proximal end of the shaft has a greater rigidity than the distal end. The tube includes an inflatable cuff at the distal end. Upon inflation, the cuff forms a seal between the shaft and an interior wall of the trachea, thereby permitting at least the low rigidity distal end of the shaft to self-center within the trachea.

18 Claims, 3 Drawing Sheets

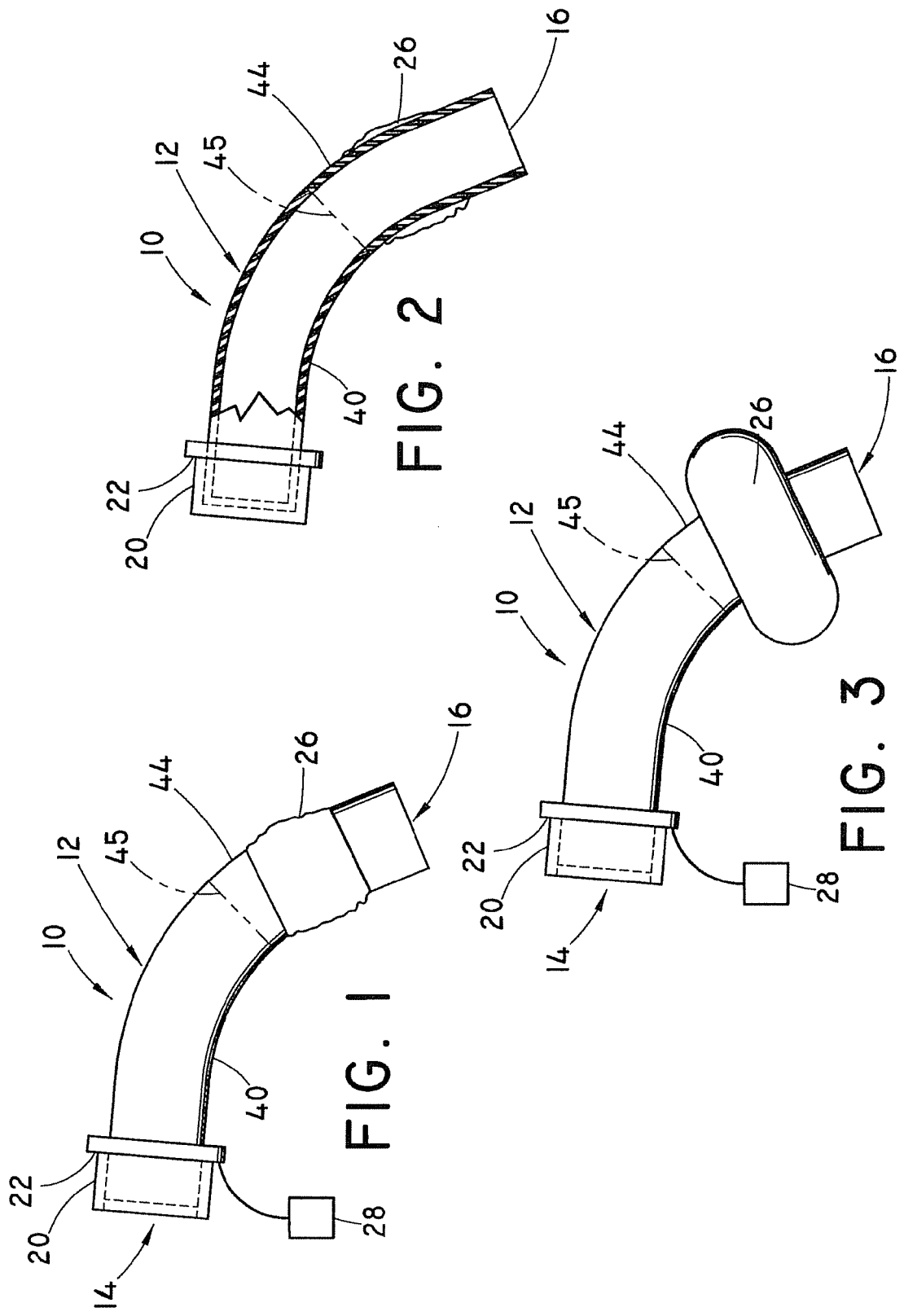

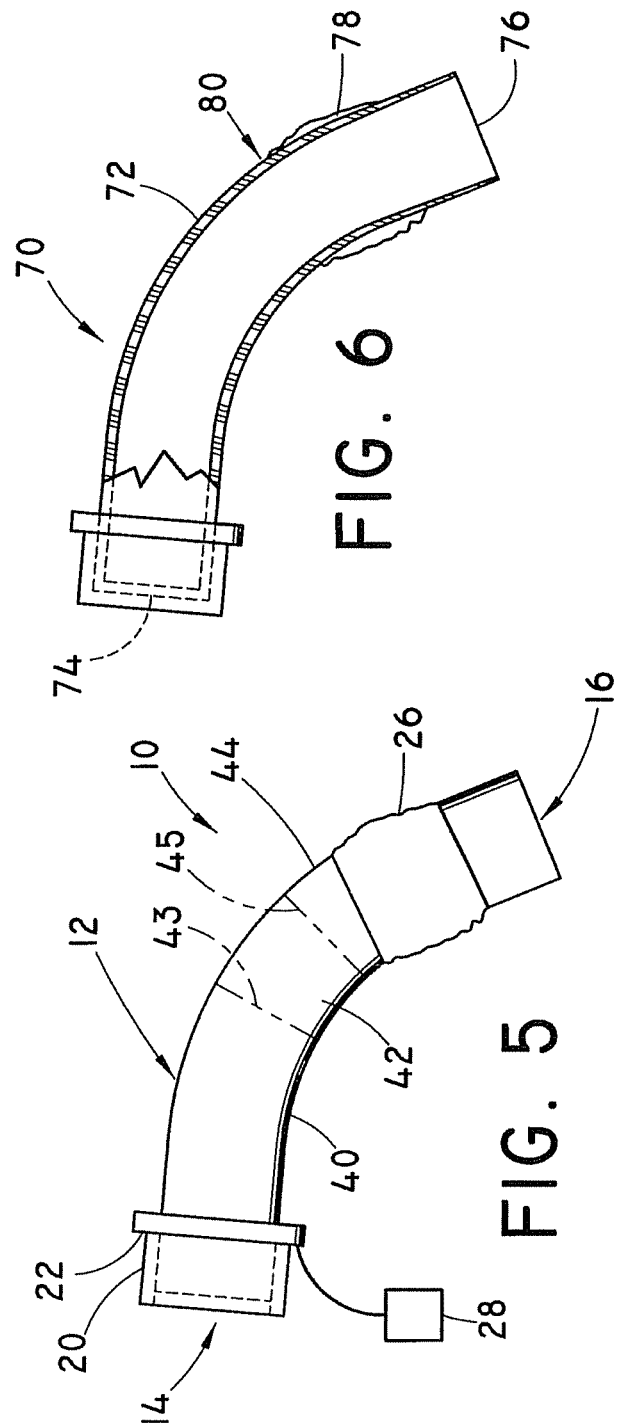

SELF-CENTERING TRACHEOSTOMY TUBE

BACKGROUND

1. Technical Field

The present application relates generally to airway management devices, and more particularly, to a tracheostomy tube having means for maintaining the tube in the center portion of the trachea.

2. Background Information

The restoration of an adequate air passageway is the first critical step in maintaining the ability of a seriously ill or injured patient to breathe, or in performing resuscitation on a patient unable to breathe. Endotracheal intubation (the placement of a tube through the nostrils or mouth and into the trachea itself) is a preferred method for establishing an air passageway when the trachea, nostrils and/or mouth are free of obstruction. When such obstruction is present, however, endotracheal intubation is generally not possible. In such cases, some other passageway must be established to provide adequate airflow to the patient.

The most direct way to provide an air passageway under these circumstances is to form an opening in the tracheal wall, and once formed, to maintain the opening by inserting a tracheostomy tube therethrough. A ventilating fluid, such as air or oxygen, is then passed through the tube to the interior of the trachea. Conventional tracheostomy tubes generally are formed of a relatively stiff polymeric composition, such as polyvinyl chloride (PVC). The tube typically includes a permanent bend along its length, and is configured such that an open distal end of the tube points downwardly into the trachea. A circumferential inflatable cuff provides a seal between the interior tracheal wall and the tracheostomy tube at a location proximal to the distal opening of the tube. The distal opening provides a passageway for air into the lungs of the patient. The seal prevents the intrusion of blood, tissue or foreign matter into the lower trachea, bronchi and lungs, while permitting control and monitoring of the airflow established through the tracheostomy tube.

Although procedures for placement of a conventional tracheostomy tube are well known, those skilled in the art will appreciate that the tracheostomy tube is inserted into sensitive and crucial areas of the body's respiratory system. Once placed within the trachea, a tracheostomy tube often remains in place for many months. If the tube is not properly centered in the trachea, or if it becomes off-centered during the passage of time, damage to the anterior and/or posterior wall of the trachea may result. In addition, an off-centered tracheostomy tube is often poorly functional.

It is desired to provide a tracheostomy tube that avoids the problems of the prior art, and that includes a means for self-centering the tube within the trachea.

BRIEF SUMMARY

The problems of the prior art are addressed by the self-centering tracheostomy tube of the present invention. In one form thereof, the present invention is directed to a tube for use in providing an air passageway through an opening in a tracheal wall of a patient. The tube includes a shaft having a proximal end and a distal end, and a curve along a length of the shaft. At least the distal end and the curve are sized for passage through the opening into an interior space of the trachea of the patient. The proximal end has a first rigidity and the distal end has a second rigidity, wherein the first rigidity is greater than the second rigidity. The tube may include an inflatable cuff at the distal end. Upon inflation the cuff forms a seal between the shaft and an interior wall of the trachea, thereby permitting at least the distal end of the shaft to self-center within the trachea.

In another form thereof, the present invention is directed to a tube for use in providing an air passageway through an opening in a tracheal wall of a patient. The tube includes a shaft having a proximal end and a distal end, and a curve along a length of the shaft. At least the distal end and the curve are sized for passage through the tracheal wall opening into an interior space of the trachea of the patient. At least a segment of the distal end of the shaft has a gradually decreasing rigidity toward a distal opening of the shaft. An inflatable cuff is disposed at the distal end of the shaft. Upon inflation the cuff is sized to form a seal between the shaft and an interior surface of the trachea. The distal end has a rigidity such that a position of the distal end within the trachea is responsive to inflation of the cuff.

In yet another form thereof, the present invention is directed to a method for providing an air passageway through an opening in the tracheal wall of a patient. A tracheostomy tube comprising a shaft having a proximal end and a distal end, and a curve along a length of the shaft is provided. The shaft has a proximal opening at the proximal end and a distal opening at a terminal portion of the distal end. At least the distal end and the curve are sized for passage through the tracheal wall opening into an interior space of the trachea of the patient. The shaft has an inflatable cuff at the distal end, wherein the cuff upon inflation is sized to form a seal between the shaft and an interior wall of the trachea. The proximal end has a first rigidity and the distal end has a second rigidity, wherein the first rigidity is greater than the second rigidity. The rigidity of the distal end is such that a positioning of the distal end within the trachea is responsive to inflation of the cuff. At least the distal end and the curve of the shaft are inserted through the tracheal wall opening, and positioned such that the distal opening is downwardly disposed within the trachea. The cuff is inflated to form the seal between the shaft and the trachea interior wall, whereupon the lower rigidity distal end centers within the trachea.

Other details of the invention and its preferred embodiments are provided in the following drawings, description and claims.

BRIEF DESCRIPTION OF THE DRAWINGS

FIG. 1 is a side elevation view of a tracheostomy tube according to an embodiment of the present invention, wherein the inflation cuff is in a non-inflated condition;

FIG. 2 is a longitudinal sectional view of the tracheostomy tube of FIG. 1;

FIG. 3 is a side elevation view of the tracheostomy tube of FIG. 1, wherein the cuff is inflated;

FIG. 5 is a side elevation view of an embodiment of the inventive tracheostomy tube having a section of intermediate durometer; and FIG. 6 is a longitudinal sectional view of another embodiment of a self-centering tracheostomy tube.

DETAILED DESCRIPTION OF THE DRAWINGS AND THE PRESENTLY PREFERRED EMBODIMENTS

Figure 4:
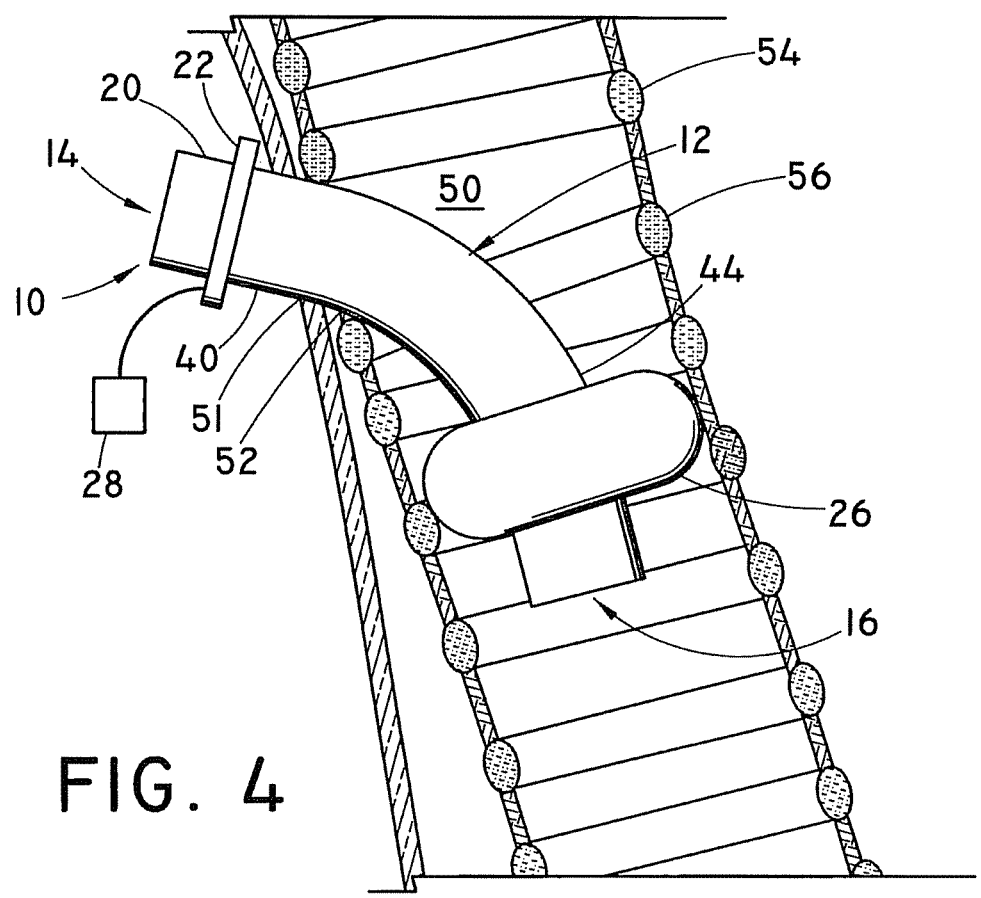
FIG. 4 is a sectional view through the tracheal wall of a patient illustrating the tracheostomy tube of the embodiment of FIG. 1 positioned therein and having the cuff inflated.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

FIG. 1 is a side elevation view of a tracheostomy tube 10 according to one embodiment of the present invention. Tracheostomy tube 10 includes a curved shaft portion 12 having a proximal opening 14 and a distal opening 16. Providing a curve along the length of shaft portion 12 facilitates introduction of the tracheostomy tube into an ostomy that has been previously formed through the tracheal wall by well-known means.

When tracheostomy tube 10 is positioned across the tracheal wall (FIG. 4), proximal opening 14 remains exterior to the patient's body. Proximal opening 14 is adapted for receiving a ventilation fluid, e.g. air or oxygen, from an external source. An optional coupling 20 of well-known configuration may be fitted over shaft proximal opening 14. Coupling 20 is sized and shaped for engagement with a mating coupling (not shown) extending from the external fluid source. A conventional flange 22 may be provided near the proximal opening for securing the tracheostomy tube 10 about the neck of the patient. Flange 22 is diagrammatically represented herein as a flat disk, but can alternatively be a conventional swivel neck plate that is capable of pivoting with respect to the shaft portion 12 of the tracheostomy tube. The use of an external fluid source, couplings, and a flange in connection with a tracheostomy tube are well known in the art, and further discussion of these features is not required to gain an understanding of the present invention.

Tracheostomy tube distal opening 16 is downwardly disposed within the trachea for transmitting the ventilation fluid in the direction of the patient's lungs. An inflatable circumferential cuff 26 is positioned proximal to distal opening 16. Cuff 26 is shown in a noninflated condition in FIG. 1, and in an inflated condition in FIG. 3. Cuff 26 is of conventional construction, and is typically a thin wall, high volume, low pressure cuff, composed of a somewhat elastic material. A supply 28 of low pressure fluid (such as air) for inflating and deflating cuff 26 is represented diagrammatically in the figures. Supply 28 may include not only a fluid source or reservoir (not shown), but also any conventional tubes, bores, or conduits employed to establish fluid communication between supply 28 and cuff 26. The nature of such elements is well known, and further discussion is not required to gain an understanding of the present invention. When fully inflated, cuff 26 establishes a secure seal between the shaft and the interior tracheal wall proximal to the distal opening 16. In addition, the inflated cuff prevents the intrusion of blood, tissue or foreign matter into the lower trachea, bronchi and lungs.

Due primarily to the presence of the curve in shaft portion 12, the distal opening 16 of the tracheostomy tube may not be centered once the tube has been positioned within the trachea. Lack of centering of the distal opening can result from a multiplicity of different factors, such as the size and/or shape of the tracheostomy tube itself, the manner in which the tracheostomy tube has been inserted, and the size and shape of the tracheal wall of the patient. If the distal portion of the shaft is not centered, damage to the tracheal wall may occur, which damage will primarily result from extended contact of the tube with the anterior and/or posterior tracheal wall. Since tracheostomy tubes may be positioned within the trachea for several weeks or even months, extended contact with the tracheal wall can cause trauma to the lining of the wall. In addition, an off-centered or poorly centered distal opening may detract from proper functioning of the tracheostomy tube.

The present invention includes a mechanism for centering the distal opening of tracheostomy tube in the trachea. Unlike prior art tracheostomy tube shafts which are generally formed from a substantially rigid material, the shaft of the inventive tracheostomy tube comprises respective proximal and distal ends formed from materials having different durometers. The term "durometer" is used here in its conventional sense to refer to the hardness of a material. A higher durometer indicates a harder, more rigid material, whereas a lower durometer indicates a softer, more flexible material.

The tracheostomy tube 10 of the present invention can be formed of conventional materials commonly utilized for such purposes, such as PVC, urethanes, and polyamides (nylons). The proximal end 40 of the tracheostomy tube is formed of a relatively high durometer material. Preferably, the proximal end will have a durometer of between about 60 and 100 on the Shore A scale. Use of the higher durometer material at the proximal end facilitates placement (pushability) of the tube, and enhances its kink resistance. The distal end 44 of the tube is formed of a lower durometer material. Preferably, the distal end will have a durometer between about 40 and 70 on the Shore A scale. This results in a distal end that is softer and more flexible than the proximal end. Those skilled in the art will appreciate that the respective proximal and distal ends need not necessarily be formed of the same base polymer, as long as the compositions of the respective ends are capable of bonding, adhering or otherwise be capable of attachment to each other as described herein.

Those skilled in the art will appreciate that the durometer ranges provided above are only examples of suitable durometers, and that higher, or lower, values may be appropriate for a particular case. If desired, conventional radiopaque agents can be added to enhance the radiopacity of part, or all, of the tube in well-known fashion. Typically, a radiopaque agent may be added to the distal end of the tube.

In a preferred embodiment, tracheostomy tube proximal end 40 extends from proximal tube opening 14 to an area just proximal of the cuff, in this case junction 45 with distal end 44. Distal end 44 extends from junction 45 to distal tube opening 16. This is best shown in the sectional view of FIG. 2. Providing a softer, more flexible distal end 44 allows that end of the tracheostomy tube to more easily adjust, or re-adjust, in response to pressures or forces exerted on tube distal end 44 that might otherwise result in an off-center positioning of the distal end. Due to the more flexible construction of distal end 44 as noted when compared to the more rigid proximal end, the distal end is capable of being re-centered within the trachea responsive to such pressures or forces. The exact location of the junction between the proximal end distal ends is typically not critical, and a low durometer distal end of greater or lesser length than indicated in the figures can be created.

Preferably, the high durometer proximal end comprises the major length of the shaft, and the low durometer distal end comprises a lesser length. Thus, for example, the high durometer proximal end 40 may have a length between about 3 and 6 cm. The low durometer distal end 44 may have a length between about 1 and 3.5 cm. Those skilled in the art will appreciate that the lengths provided above are only examples of suitable lengths, and that longer, or shorter, lengths may be appropriate for a particular case.

The respective proximal and distal ends 40, 44 may be bonded, or adhered, to each other along the length of shaft 12 by any conventional means, such as thermal bonding or adhesion. Attachment of distal ends to elongated portions of medical devices is a well known technique in the art, and a skilled artisan can readily determine an acceptable attachment mechanism without undue experimentation. For example, the adjoining edges of the respective end portions to be joined can be directly bonded to each other. Alternatively, the adjoining edges can be mutually tapered, slotted, or otherwise configured in well-known fashion to mate in a manner to enhance the attachment therebetween.

FIG. 4 illustrates tracheostomy tube 10 positioned within the trachea 50 of the patient. Tracheostomy tube 10 is inserted through an incision 51 formed in the skin of the patient, and thereafter through a tracheal entrance 52 between adjacent tracheal rings, in this case rings 54, 56. Once inflated, cuff 26 spans the area between the outer wall of tracheostomy tube 10 and the interior tracheal wall to form a seal. Distal opening 16 communicates with the interior space of trachea 50 downward from cuff 26. The flexibility of distal end 44 is such that the distal end is able to conform to the position of the cuff, and thereby self-center within the trachea.

Although a tracheostomy tube 10 having distinct proximal and distal end portions 40, 44 of different durometers is illustrated herein in FIGS. 1-4, the invention is not limited to the specific arrangement shown and described. For example, tracheostomy tube 10 may include one or more intermediate sections having respective durometer(s) intermediate the durometers of respective proximal and distal ends 40, 44. Utilizing one or more intermediate sections will generally provide a more gradual reduction in durometer from the proximal end to the distal end.

FIG. 5 illustrates tracheostomy tube 10 as shown and described, but including an intermediate section 42 between respective proximal end distal ends 40, 44. Junction 43 separates proximal end 40 and intermediate section 42. The remaining portions of the tracheostomy tube shown in FIG. 5 correspond to analogous features illustrated in FIG. 1, and have therefore been provided with the same reference numbers utilized in FIG. 1. If desired, additional intermediate sections may be added if an even more gradual reduction in durometer is desired. Preferably, the respective durometers of any such intermediate sections are selected such that a gradual reduction in durometer occurs from highest durometer at the proximal end to lowest durometer at the distal end. When one or more intermediate sections are included, the various segments of the shaft may be broken down into any convenient proportion of the total length of the shaft. The various sections may be attached by any conventional means, such as the aforementioned thermal bonding or adhesion.

An alternative way of forming a tracheostomy tube according to the present invention is by a continuous extrusion process. Continuous extrusion processes are known in the art and enable the continuous extrusion, without bonding, of a tubular shaft having portions of different durometer. With continuous extrusion, a tracheostomy tube shaft can be extruded to have a higher rigidity at one end and a higher flexibility at the other end. The shaft can be extruded by known means to provide a gradual durometer decrease over a defined length of the shaft, such as the distal end of the shaft, or along the entire length of the shaft if desired. Alternatively, the shaft can be extruded to provide as many segments having a gradual durometer decrease as desired.

With continuous extrusion, the shaft can be formed to eliminate areas of high stress that may otherwise result when high and low durometer segments are joined together. When various shaft segments are bonded or otherwise joined in a manner that results in creating high stress areas, the shaft segments may break or separate during use of the tracheostomy tube. This possibility is minimized when the various lengths of the shaft are continuously extruded as described. A continuously extruded shaft may be formed from a single polymer having different durometers, or alternatively, by altering the properties of a particular polymer used along the length of the shaft.

In addition to extruding sections of different durometers, continuous extrusion techniques may also be used to extrude a shaft having one or more segments that differ from one another in the type of polymer that is extruded, and/or in other properties of the shaft, such as the level of radiopacity. When the shaft is formed to have segments of different levels of radiopacity, the physician can more clearly distinguish certain parts of the shaft from other parts under conventional imaging techniques, such as x-ray fluoroscopy. One preferred continuous extrusion process is referred to as Total Intermittent Extrusion (TIE), developed by Putnam Plastics Corporation of Dayville, Conn.

FIG. 6 illustrates a sectional view of another alternative embodiment of the present invention. This embodiment illustrates a sectional view of a portion of a tracheostomy tube 70 having a curved shaft portion 72, and respective proximal and distal openings 74, 76. An inflatable cuff 78 is provided as before. In this embodiment, the wall of the shaft has a gradually decreasing thickness toward the distal end. Preferably, the wall thickness decreases along distal end 80 from a portion just proximal of cuff 78 to distal opening 76. Formation of a device having a wall with a gradually reduced thickness is known in the art, and any convenient manner of reducing the thickness of a segment may be utilized. Methods for reducing the thickness of a shaft in this manner include, among others, grinding, buffing, heat tapering or pulling down. In addition, the wall thickness can also be controllably reduced during extrusion of the shaft in well-known fashion.

Those skilled in the art will appreciate that reducing the thickness of a portion of the shaft wall increases the flexibility of the reduced-thickness portion. In theory, the reduced thickness portion can originate anywhere along the length of the shaft, however in order to retain the strength and pushability of the shaft, it is preferred to limit the reduced thickness segment to the distal end portion as described. The flexibility of this reduced diameter portion of the tracheostomy tube shaft provides benefits similar to those obtained by providing a low durometer distal end portion as described above.

As a variation of the embodiment of FIG. 6, instead of an integral shaft having a reduced thickness distal end portion as described, the shaft may comprise two bonded shaft segments. In this variation, the proximal end may comprise a portion of constant wall thickness, and the distal end having the gradually reduced diameter can be bonded or otherwise attached to the proximal end portion. As a still further variation, one or more transition segments of intermediate wall thickness may be positioned between the respective proximal and distal ends.

It is therefore intended that the foregoing detailed description be regarded as illustrative rather than limiting, and that it be understood that it is the following claims, including all equivalents, that are intended to define the spirit and scope of this invention.

What is claimed is:

1. A self-centering tracheostomy tube, comprising:
   a shaft having a proximal end and a distal end, and a curve along a length of said shaft, at least said distal end and said curve configured and arranged for passage through an opening in a tracheal wall into an interior space of the trachea of the patient; and a cuff disposed at said shaft distal end, said cuff inflatable upon passage through said wall to form a seal between the shaft and an interior surface of the trachea, said shaft distal end having a lower rigidity than a rigidity of said proximal end, such that a position of said distal end relative to said proximal end in the trachea self-centers in said trachea in response to inflation of said cuff, said proximal end has a durometer between about 60 and 100 on the Shore A scale, and the distal end has a durometer between about 40 and 70 on the Shore A scale, wherein at least a portion of said curve comprises said distal end durometer, and wherein said cuff is fully disposed along said distal end.

2. The self-centering tracheostomy tube of claim 1, wherein said proximal end and said distal end are securely engaged at adjacent edges by one of bonding and adhesion, said proximal end having a length between about 3 and 6 cm, and said distal end having a length between about 1 and 3.5 cm.

3. The self-centering tracheostomy tube of claim 1, wherein one of said proximal and distal ends includes a radiopaque agent, and the other of said ends is free of said radiopaque agent.

4. The self-centering tracheostomy tube of claim 1, wherein said shaft includes at least one intermediate section disposed along a length of said shaft between said proximal end and said distal end, said at least one intermediate section having a rigidity less than the rigidity of the proximal end and greater than the rigidity of the distal end.

5. The self-centering tracheostomy tube of claim 1, wherein said distal end has a wall thickness less than a wall thickness of said proximal end.

6. The self-centering tracheostomy tube of claim 1, wherein at least a portion of said distal end has a gradually decreasing wall thickness toward a distal opening of said tube.

7. The self-centering tracheostomy tube of claim 1, wherein said proximal end is formed from a first polymer, and said distal end is formed from a second polymer, said first polymer having a greater length along said tube than said second polymer.

8. A tube for use in providing an air passageway through an opening in a tracheal wall of a patient, comprising:
a shaft having a proximal end and a distal end, and a curve along a length of said shaft, at least said distal end and said curve sized for passage through said tracheal wall opening into an interior space of the trachea of the patient, at least a segment of said distal end of said shaft having a gradually decreasing rigidity toward a distal opening of said shaft, a cuff disposed at said distal end, said cuff inflatable from a non-inflated condition to an inflated condition, said cuff upon inflation sized to form a seal between the shaft and an interior surface of the trachea, said distal end rigidity being such that said distal end self-centers within said trachea is responsive to inflation of said cuff, said proximal end has a durometer between about 60 and 100 on the Shore A scale, and the distal end has a durometer between about 40 and 70 on the Shore A scale, wherein at least a portion of said curve comprises said distal end durometer, and wherein said cuff is fully disposed along said distal end.

9. The tube of claim 8, wherein said shaft has a gradually decreasing rigidity from said proximal end to said distal end.

10. The tube of claim 9, wherein said gradually decreasing rigidity comprises a continuous extrusion of said shaft.

11. The tube of claim 10, wherein a length of said continuous extrusion includes an agent capable of providing a level of radiopacity, and another length of said continuous extrusion does not include an agent capable of said level of radiopacity.

12. The tube of claim 8, wherein said proximal end comprises a first polymer and said distal end comprises a second polymer.

13. A method for positioning a tracheostomy tube in the trachea of a patient, comprising:
aligning a tracheostomy tube for insertion through an opening in the tracheal wall, said tracheostomy tube comprising a shaft having a proximal end and a distal end, and a curve along a length of said shaft, said shaft having a proximal opening at said proximal end and a distal opening at a terminal portion of said distal end, at least said distal end and said curve sized for passage through said tracheal wall opening into an interior space of the trachea of the patient, said shaft having a cuff at said distal end, said cuff inflatable from a non-inflated condition to an inflated condition, said cuff upon inflation sized to form a seal between the shaft and an interior wall of the trachea, said proximal end having a first rigidity and said distal end having a second rigidity, said second rigidity being lower than said first rigidity, said distal end rigidity being such that a position of said distal end within said trachea is movable relative to a position of said proximal end responsive to inflation of said cuff, said proximal end has a durometer between about 60 and 100 on the Shore A scale, and the distal end has a durometer between about 40 and 70 on the Shore A scale, wherein at least a portion of said curve comprises said distal end durometer, and wherein said cuff is fully disposed along said distal end;
inserting at least said distal end and said curve through said opening in said tracheal wall, and positioning said distal end such that said distal opening and said cuff are downwardly disposed within the trachea; and
centering said distal end and said distal opening of the shaft in the interior space of the trachea by inflating said cuff for forming said seal between the shaft and the trachea interior wall, wherein upon inflation of said cuff and formation of said seal, a position of said lower rigidity distal end self-adjusts relative to said proximal end within the trachea.

14. The method of claim 13, wherein said proximal end and said distal end are securely engaged at adjacent edges by one of bonding and adhesion.

15. The method of claim 13, wherein one of said proximal and distal ends includes a sufficient quantity of a radiopaque agent such that said one end is visible under x-ray fluoroscopy, and the other end is at least substantially free of said radiopaque agent, such that a radiopaque contrast is visible between said ends.

16. The method of claim 13, wherein said distal end has a wall thickness less than a wall thickness of said proximal end.

17. The method of claim 13, wherein at least a segment of said distal end of said shaft has a gradually decreasing rigidity toward a distal opening of said shaft.

18. The method of claim 17, wherein said shaft has a gradually decreasing rigidity from said proximal end to said distal end.

* * * * *